United States Patent [19]

Wielinger et al.

[11] 4,250,256

[45] Feb. 10, 1981

[54] MICROBIOLOGICAL TEST DEVICE

[75] Inventors: Hans Wielinger; Walter Rittersdorf; Manfred Bleisteiner, all of Mannheim; Gerd Zimmermann, Weinheim; Wolfgang Werner; Wolfgang Vömel, both of Mannheim, all of Fed. Rep. of Germany

[73] Assignee: Boehringer Mannheim GmbH, Mannheim, Fed. Rep. of Germany

[21] Appl. No.: 44,629

[22] Filed: Jun. 1, 1979

[30] Foreign Application Priority Data

Jun. 12, 1978 [DE] Fed. Rep. of Germany ....... 2825636

[51] Int. Cl.$^3$ .............................................. C12Q 1/18
[52] U.S. Cl. ........................................ 435/32; 422/58; 435/33; 435/34; 435/39; 435/40; 435/292; 435/293; 435/299; 435/300; 435/301; 435/805; 435/810

[58] Field of Search ....................... 435/29, 30, 31, 32, 435/33, 34, 35, 36, 37, 38, 39, 40, 292, 293, 294, 295, 296, 299, 300, 301, 805, 810; 422/58

[56] References Cited

U.S. PATENT DOCUMENTS

| 2,904,474 | 9/1959 | Förg | 435/30 X |
|---|---|---|---|
| 3,000,706 | 9/1961 | Royce | 435/31 X |
| 3,802,842 | 4/1974 | Lange et al. | 435/805 X |
| 3,814,670 | 6/1974 | Frecke et al. | 435/30 X |
| 3,881,993 | 5/1975 | Frecke et al. | 435/30 X |
| 4,066,511 | 1/1978 | Montagnon | 435/34 |

Primary Examiner—Robert J. Warden
Attorney, Agent, or Firm—Sprung, Felfe, Horn, Lynch & Kramer

[57] ABSTRACT

Microbiological test device having a nutrient card or cards and a covering layer thereover which is permeable to nutrients but impermeable to bacteria. The covering layer is made from an aqueous dispersion of a water insoluble resin and a pore former.

25 Claims, 2 Drawing Figures

MICROBIOLOGICAL TEST DEVICE

BACKGROUND

This invention relates to a device for microbiological purposes which includes a nutrient card and a film made from a synthetic resin dispersion lying thereabove, the nutrient card and the dispersion film being combined to form a test unit.

The investigation of certain body fluids for the presence of micro-organisms, such as the detection of bacteria and fungi in urine, provides the physician, microbiologist and the like with valuable indications for the diagnosis of particular diseases. Consequently, numerous test means have been developed in recent years for the detection of bacteria and fungi.

However, detection means of this type are also used for the investigation of pharmaceuticals, foodstuffs, water, swimming pools and the like where certain kinds of microorganisms are harmful or can constitute a danger to health.

The known processes of culturing and detecting microorganisms depend upon the fact that various selected nutrients and possibly selectively inhibiting agents are worked up with agar-agar to give a nutrient medium. Although nutrient media are important for special problems, they are disadvantageous for routine operations, especially when cost-saving and comparatively large numbers of samples are to be investigated. The nutrient media must be prepared by the user in a relatively laborious manner from a dry powder. Nutrient media ready for use are also commercially available in swollen form. However, nutrient agar media which are ready for use readily dry out and can then no longer be reversibly moistened, which means that they must be packed in moisture-proof packings which, in addition, take up a large volume.

More recently, especially for the investigation of foodstuffs and water, microbiological detection processes have been described in which nutrient cards are covered with membrane filters. For this purpose, the liquid to be investigated is filtered through a membrane filter, the membrane filter is laid upon a nutrient card moistened with sterile water or upon a filter card impregnated with sterile nutrient solution and this unit then cultured in a Petri dish. The micro-organisms retained on the membrane filter grow during the incubation period and become visible as colonies.

This process is only practicable when micro-organisms are to be detected in very small concentrations and, therefore, must be enriched before detection by means of incubation. The membrane filters and nutrient cards are provided loose and, because of the brittleness of the membrane material, require especially careful handling. An improvement is provided by combining the membrane filter and the nutrient card into a single unit in a special frame (see German Pat. No. 2,115,674). This process admittedly simplifies handling but the production of the unit comprising the membrane filter and the nutrient card in a special frame is laborious and expensive.

The described filter processes are not suitable for medical diagnostic problems since a concentration of the micro organisms on the surface of the filter is not necessary and, indeed, because of the necessity of distinguishing high micro-organism counts, preferably in the range of from $10^3$ to $10^8$ micro-organisms per ml. of body fluid, is of great disadvantage.

Furthermore, processes are known in which a microporous membrane is produced on a nutrient card in such a manner that the membrane material partly penetrates into the card (see German Pat. No. 2,320,946). This process suffers from the disadvantage that the surface of the membrane has the same roughness or unevenness as that of the nutrient card. In the case of such a test, because of the unevenness of the surface, the micro-organisms are, without additional means, not visible at all or very poorly visible after the incubation. They must be rendered visible by coloring with dyestuffs. Therefore, the micro-organisms appear in a completely different manner to the viewer than in the case of the well-known detection processes on agar-agar. A visual differentiation of the species is not possible. The colonies, which penetrate more or less into the nutrient card, cannot be separately used for inoculation. However, such an inoculation is absolutely essential for a differentiation of micro-organisms and for an investigation of resistance behavior.

Another process is known which is essentially a further development of the above-described process, it having the object of overcoming the disadvantages of this process. This test, which is described in German Pat. No. 2,320,943, is improved in that, instead of the membrane layer or above the membrane layer, there is applied a gel layer, the gel layer and the nutrient card passing over into one another. It is thereby preferable also to incorporate nutrients into the gel layer. As is known from experience, such gel layers cannot be applied to paper surfaces with the same uniformity and smoothness as is possible in the case of swollen agar layers. Therefore, this process suffers from disadvantages which are similar to those possessed by the process according to German Pat. No. 2,320,946.

SUMMARY

The present invention provides a dry nutrient substrate for micro-organisms which, upon dipping into a micro-organism-containing liquid to be investigated, takes up water with appropriate rapidity and the surface of which, in a moist state, is as smooth and uniform as that of the well-known agar media. The micro-organisms remains on the surface in the case of dipping into a micro-organism-containing solution, in an amount equivalent to their concentration. The micro-organisms, within the usual incubation period (12 to 24 hours), forms colonies as is the case with the well-known agar nutrient media. Thus, with these dry nutrient substrates, the number of micro-organisms and the species thereof are capable of determination in the same manner as in the case of the well-known processes. Furthermore, it is possible to test the resistance behavior of the micro-organisms.

To accomplish this, it was necessary to develop special covering layers for the nutrient card which did not exhibit the disadvantages of the above-described processes.

It has been found that films based upon synthetic resin dispersions provide a satisfactory solution to the problem. For this purpose, synthetic resin films are provided with a "pore former" which imparts the following properties to films produced from the dispersions:

the film remains impermeable to micro-organisms;

the film is permeable to bacterial nutrients and to substances which selectively or generally inhibit or suppress the growth of micro-organisms;

the surface of the film is smooth;

on the surface of the film, the micro-organisms are firmly held corresponding to their concentration in the medium to be investigated.

Thus, according to the present invention, there is provided a device for microbiological purposes, comprising a nutrient card and a covering layer which is impermeable to bacteria but permeable to nutrients, wherein the covering layer consists of a water-insoluble synthetic resin film modified with a pore former, said film having been produced from an aqueous dispersion of the synthetic resin.

DESCRIPTION OF THE DRAWING

The present invention will be more fully understood in view of the following description taken in conjunction with the accompanying drawing wherein.

DESCRIPTION

Figure 1:
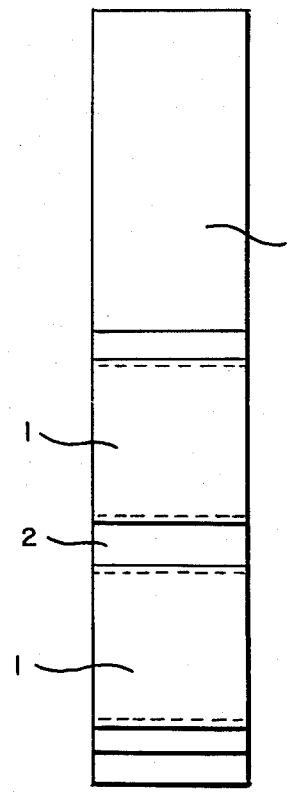
FIG. 1 is a side view of a test device according to the invention wherein nutrient cards 1 mounted on a handle/carrier 3 are covered with a film 2.

As dispersion materials, there can, in principle, be used all aqueous synthetic resin dispersions, with the proviso that the films formed from these dispersions do not have a negative effect on bacterial growth. Thus, for example, the following dispersions can be employed: homopolymers of vinyl acetate, acrylic acid esters and the like; co-polymers of vinyl propionate and vinyl acetate, vinyl propionate and vinyl chloride, vinyl acetate and maleic acid esters, acrylic acid esters with acrylonitrile and vinyl propionate, butadiene and styrene and the like.

As pore formers, there can, in principle, be used all water-soluble or water-swellable compounds which do not have a negative effect on bacterial growth, which dissolve or swell in the moistened film only to such an extent that the structure of the film is not so destroyed that the film breaks down or such large holes are formed that the micro-organisms can pass through. If they are metabolized, then such metabolism must not provide the micro-organisms with the possibility of being able to pass through the film or of destroying the structure thereof to such an extent that the colonies are no longer clearly visible.

Of course, mixtures of substances which have pore forming properties can also be used. In special cases, the use of several pore formers in a film can be advantageous.

As pore formers there can preferably be used the following macromolecular substances: polyethylene glycols, polyethylene oxides, polyvinylpyrrolidone, polyvinyl alcohols, partially saponified polyvinyl esters, co-polymers of vinyl-pyrrolidone and vinyl esters, cellulose derivatives, such as hydroxyalkylcelluloses, and the like. Furthermore, there can also be used low molecular weight materials, such as sugars, nutrient salts and the like, as well as mixtures of such macro- and micro-molecular materials.

In the composition of the formulation of the crude film mass, the addition of wetting agents is of advantage. In this way, not only are the properties of the film improved but also the growth of certain species is selectively influenced and an undesired behavior of the micro-organisms during the incubation phase, for example clustering of Proteus, is prevented. As wetting agents, there can be used all substances conventionally employed in microbiology, for example sodium dodecyl sulfate, sodium heptadecyl sulfate, N-cetyl-N,N,N-trimethyl-ammonium bromide, polyoxyethylene sorbitan monooleate and the like.

Since the growth of the micro-organisms is also decisively dependent upon the pH value of the medium on or in which they grow, with the help of conventional buffers, for example Sorensen buffer, the pH value of the film mass is adjusted to the desired range. The salt concentration is thereby selected in such a manner that the osmolar conditions correspond to the requirements for a satisfactory micro-organism growth.

In addition to the pore formers (macromolecular compounds), wetting agents and buffers, the films can also have incorporated therein selective inhibiting materials or antibiotics so that, by means of such a formulation, the growth of micro-organisms can be selectively inhibited or the minimum inhibiting concentration of antiobiotics can be determined.

Films of this type are produced in known manner as follows:

The synthetic resin dispersion is homogeneously stirred with a solution of the pore former. Into this mixture are stirred the other components, such as wetting agent, buffer, inhibiting materials and the like. In these crude film masses, the weight ratios of the dispersion polymer to the pore former can vary from 50:1 to 1:5. The addition of solvents depends upon the desired viscosity of the mass which, depending upon the method to be used for further working up, can vary very greatly. The concentrations of the remaining additives depend upon the requirements which they are to satisfy and they can be from 0 to 15% and preferably from 1 to 5% of the synthetic resin covering layer.

The films themselves are produced in the usual manner in that the crude film mass is coated, scraped, sprayed or the like, in a layer thickness of from 10 to 1000$\mu$, onto a substrate with which the crude film mass does not bind too firmly. After or during drying, the film is pulled or lifted off from the substrate and subsequently further worked up.

In order to stabilize films against stretching in the longitudinal or transverse direction, they can be produced by applying crude film mass in known manner onto an inner carrier, for example a woven or knitted material or the like, which lies upon an inert substrate. Preferred carriers are commercially available synthetic resin meshes of polyamide, polyester, polyethylene or the like which are known, for example, as bolting cloth and have, for example, a thickness of about 10 to 200$\mu$.

Such supported films can also be produced by impregnating or coating the inner carrier with the film mass, whereafter, by wiping off or the like, the film thickness can be adjusted. If such films are combined with known nutrient cards to give test systems, then a test device is obtained which fully satisfies the above-mentioned requirements.

Nutrient cards can be produced in known manner by impregnating filter papers or other appropriate absorbent carrier layers with solutions of nutrient mixtures which are conventional in microbiology and subsequently dried. In this manner, a large variety of nutrient cards can be produced with various properties. Examples of nutrient media which can be used include MacConkey's nutrient medium, CLED nutrient medium, Slanetz and Bartley's nutrient medium, China blue-lactose nutrient medium, endo nutrient medium, Wilson-Blair's bismuth sulfite nutrient medium, cetrinimide nutrient medium, CaSo nutrient medium, Müller-Hinton's nutrient medium. Sabouraud's nutrient medium and the like.

The test device ready for use can be constructed in various ways. The models which have proved to be the best will now be described.

A self-supporting film or a film which is stabilized by an inner carrier is laid upon a nutrient card which is preferably a filtered paper impregnated with a nutrient solution conventionally used in microbiology and preferably contains at least one wetting agent, moisture retaining agent, swelling agent, buffer, salt and/or antibiotic. For the detection of micro-organisms, the nutrient card and the film are dipped into the micro-organism-containing solution to be investigated. Both are placed, one on top of the other, in a Petri dish and incubated for 12 to 24 hours. The micro-organisms to be detected become visible in the form of colonies in known manner.

If it is desired to quantify the number of micro-organisms, then it is preferable to produce the film in such a manner that, as inner carrier, a woven mesh is used in which, at definite distances, for example of 0.5 cm. in each direction, the filaments thereof are color marked in a different manner, the mesh thus being divided up into squares in a manner reminiscent of the engraved chamber of a haemocytometer. If such a film, together with the nutrient card, is dipped into a micro-organism-containing liquid and subsequently incubated, then, from the number of colonies per unit surface area, the number of micro-organisms per unit volume can be determined very easily. In the case of one device which is particularly easy to produce, the nutrient card is laid upon a support a stiff foil preferably a water resistant support such as a synthetic resin foil, a somewhat wider piece of the above-described test film is laid thereover and a pocket is formed by adhering, welding or sealing projecting edges of the film adjacent the nutrient card onto the foil in such a manner that the nutrient card is firmly clamped in the pocket resulting between the foil and the film. This test strip, which preferably has a width of 0.5 to 5 cm., in which the test area is preferably quadratic, is prepared for the user as follows: it is sealed or stuck between the foils or coated papers and sterilized in conventional manner. There is thus obtained a dry nutrient substrate in an extremely space-saving form. Furthermore, the nutrient substrate can be stored for a much longer period of time than a nutrient agar since it cannot dry out and the sensitive nutrient materials in the dry state are much more stable than in swollen agar. Before use, the test strip is removed from the foil packing. For the detection of micro-organisms, for example in urine, the test strip is dipped in fresh, cleanly collected middle stream urine, i.e., urine being excreted before the bladder is empty, placed in an incubation vessel and incubated. The packing can possibly also serve as an incubation vessel. On the basis of comparative tables, the number of micro-organisms per ml. of urine can be determined. It is preferable to combine a universal nutrient with several selective nutrient media and/or elective nutrient media in one test unit.

For preparation of an antibiogram, such a device which contains, for example, a universal nutrient card, for example Müller-Hinton nutrient medium, is moistened with sterile water, a slurry of the micro-organisms to be tested is applied thereto with a spatula and an antibiotic leaflet, such as is described in German Industrial Standard No. 58940, is placed thereon. After incubation, evaluation is carried out in the usual way.

Another possibility of investigating the resistance behavior of micro-organisms is the determination of the minimum inhibiting concentration (MIC) and/or minimum promoting concentration. This is determined in the following manner with an antibiotic being used as an example of an inhibiting substance:

The antibiotic in the desired concentration is incorporated directly into the film mass and test strips are produced from the films prepared therefrom. A nutrient card with a universal nutrient medium is, together therewith, placed onto a foil and the appropriate antibiotic-containing film sealed thereover in the manner described above. It is also possible to incorporate the antibiotic into the nutrient card.

Some antibiotics are only stable for a comparatively long period of time in a relatively narrow pH range, this pH range being one which does not necessarily correspond to the optimum pH for the growth of the micro-organisms. For the determination of the MIC of such substances by the process according to the present invention, the films are produced in the following manner and further worked up to give test strips in the manner described above.

Onto one of the above-described antiobiotic-free films there is applied a second film which contains the desired antibiotic. The buffer capacity of the second film is adjusted in such a manner that, upon dipping into the aqueous sample material to be investigated, the buffer of the first film or of the nutrient medium ensures the adjustment of the pH value to one which is optimum for the growth of the micro-organism. The second film can be produced from the same crude film mass as the first film, except that it must have a different pH value corresponding to that desired for the antibiotic. However, it is not necessary that the synthetic resin dispersion and the opener are identical in both films.

It is also possible to produce the second film, in which the antibiotic is incorporated, from a water-soluble or water-swellable film former which is substantially inert for the growth of the micro-organisms. As film formers for this purpose, there are preferably used the same materials as can also be used as pore formers.

Furthermore, the antibiotic-containing film and the nutrient card can, of course, also have different pH values so that the buffer of the nutrient card ensures the optimum pH value for the growth of the micro-organisms only after moistening the surface of the film.

Incorporating the antibiotic directly into the film or nutrient card and incorporating it into a test unit for the determination of the MIC has the following advantages: it is no longer necessary to lay antibiotic leaflets onto an agar plate. Without the previous unavoidable intermediate step of micro-organism culturing, the resistance behavior of the micro-organisms can be tested directly from the sample material. This novel method avoids the complicated process, previously necessary for the determination of the MIC, of having to weigh out the antibiotic every time for each series of investigations. Finally, the assessment of the inhibited growth of the micro-organisms is substantially easier: it is now no longer necessary to assess the degree of turbidity of the nutrient broth: on the contrary, the growth of the micro-organisms can be evaluated directly on the surface of the film and classified thereon.

The following examples are given for the purpose of illustrating the present invention without limiting same in any manner:

EXAMPLE 1

Production of films

A large variety of different synthetic resin dispersions and pore formers can be used for the production of the films. The two components are, together with adjuvants, stirred to give a crude film mass. (The pore formers are water-soluble, relatively slightly swelling, high polymer substances).

There is demonstrated the multiplicity of combination possibilities of the raw materials which permit the production of useful films.

The pore formers are dissolved, with stirring, in water to which is added the synthetic resin dispersions in the amounts stated in the following Tables, this mixture being stirred until homogeneous. Thereafter, 1 g. of wetting agent is added thereto, the choice of wetting agent depending upon the micro-organisms which are to be detected, for example sodium dodecyl sulfate for the inhibition of gram-negative flora, polyoxyethylene sorbitan oleate as additive for the detection of Lactobacillae and for inhibiting the clumping or agglomeration of micro-organisms, sodium heptadecyl sulfate for the inhibition of gram-positive flora and in media for the enrichment of coliform micro-organisms and N-cetyl-N,N,N-trimethylammonium bromide for the selective enrichment of Pseudomonas. In addition, 1 ml. of a buffered sodium chloride solution (composition: 92 g. disodium hydrogen phosphate dihydrate, 21.1 g. potassium dihydrogen phosphate and 7.56 g. sodium chloride in 1000 ml. water) is added thereto and the pH adjusted to 6.9 to 7.5 with 0.1 N aqueous sodium hydroxide solution.

Tabulation of the amounts of dispersion, opener and water

| Dispersion: | | | |
|---|---|---|---|
| Homopolymer of acrylic acid ester | 60 g. | 50 g. | 50 g. |
| Pore former | | | |
| Hydroxypropylmethylcellulose | 4 g. | — | — |
| Copolymers of ethylene glycol and ethylene oxide | — | 18 g. | — |
| Polyvinylpyrrolidone | — | — | 24 g. |
| Water | 30 ml. | 26 ml. | 31 ml. |

| Dispersion: | | | | |
|---|---|---|---|---|
| Copolymer of butadiene and styrene | 52 g. | 74 g. | 62 g. | 62 g. |
| Pore former | | | | |
| Polyvinylpyrrolidone | 16 g. | 16 g. | — | — |
| Copolymer of ethylene glycol and ethylene oxide | — | — | 16 g. | — |
| Copolymer of vinyl acetate and vinyl pyrrolidone | — | — | — | 16 g. |
| Water | 22ml. | 22ml. | 22ml. | 47ml. |

| Dispersion: | | |
|---|---|---|
| Homopolymer of vinyl acetate | 62 g. | 62 g. |
| Pore former | | |
| Polyvinylpyrrolidone | 20 g. | — |
| Copolymer of vinyl acetate and vinyl pyrrolidone | — | 16 g. |
| Water | 26ml. | 47ml. |

| Dispersion: | | | |
|---|---|---|---|
| Copolymer of acrylonitrile, acrylic acid ester and vinyl propionate | 78 g. | 92 g. | 78 g. |
| Pore former | | | |
| Polyvinylpyrrolidone | 16 g. | 16 g. | — |
| Copolymer of ethylene glycol and ethylene oxide | — | — | 16 g. |
| Water | 22 ml. | 22 ml. | 23 ml. |

| Dispersion: | | | |
|---|---|---|---|
| Copolymer of maleic acid and vinyl acetate | 58 g. | 60 g. | 60 g. |
| Pore former | | | |
| Polyvinylpyrrolidone | 13 g. | — | — |
| Polyethylene oxide | — | 16 g. | — |
| Copolymer of vinyl acetate and vinyl pyrrolidone | — | — | 16 g. |
| Water | 18 ml. | 62 ml. | 47 ml. |

| Dispersion: | |
|---|---|
| Homopolymer of vinyl chloride | 62 g. |
| Pore former | |

| Dispersion: | | | | | | | | | | |
|---|---|---|---|---|---|---|---|---|---|---|
| Copolymer of vinyl acetate and vinyl propionate | 62 g. | 54 g. | 45 g. | 50 g. | 90 g. | 50 g. | 90 g. | 50 g. | 48 g. | 48 g. |
| Pore former | | | | | | | | | | |
| Polyethylene oxide | — | 9 g. | — | — | — | — | — | — | 4 g. | 4 g. |
| Polyvinylpyrrolidone | 16 g. | — | — | — | — | — | — | — | 14 g. | — |
| Copolymer of ethylene oxide and ethylene glycol | — | — | 22 g. | — | — | — | — | — | — | — |
| Copolymer of vinyl acetate and vinyl pyrrolidone | — | — | — | 11 g. | — | — | — | — | — | 5 g. |
| Polyvinyl alcohol | — | — | — | — | 5 g. | 5 g. | — | — | — | — |
| Partly saponified polyvinyl acetate | — | — | — | — | — | — | 5 g. | 5 g. | — | — |
| Water | 22ml. | 36ml. | 32ml. | 33ml. | 13ml. | 13ml. | 50ml. | 50ml. | 33ml. | 27ml. |

| -continued | |
|---|---|
| Polyethylene oxide | 16 g. |
| Water | 62 ml. |

| Dispersion: | |
|---|---|
| Copolymer of vinyl chloride and vinyl propionate | 52 g. |
| Pore former | |
| Polyvinylpyrrolidone | 15.7 g. |
| Water | 22 ml. |

The crude film mass is scraped on to an inert substrate in known manner with a layer thickness of 300μ and dried at a temperature of 50° to 70° C. After drying, the film is cut up into the desired size and further worked up.

EXAMPLE 2

Production of a test strip for the determination of the micro-organism count in urine and for the rough differentiation of micro-organisms 62 g. of a dispersion of a co-polymer of vinyl acetate and vinyl propionate are stirred with a solution of 16 g. polyvinylpyrrolidone in 22 ml. water. Then, as described in Example 1, 1 ml. of a buffered physiological sodium chloride solution and 1 ml. polyoxyethylene sorbitan monooleate are stirred therein and the pH adjusted to 7.3 with aqueous sodium hydroxide solution.

A nylon mesh with a thickness of 50μ is laid onto a polyethylene foil, upon which the film mass is scraped with a layer thickness of 350μ. After drying at 60° C., the supported film now obtained is stripped off from the foil and cut up into 6 cm. wide bands.

Figure 2:
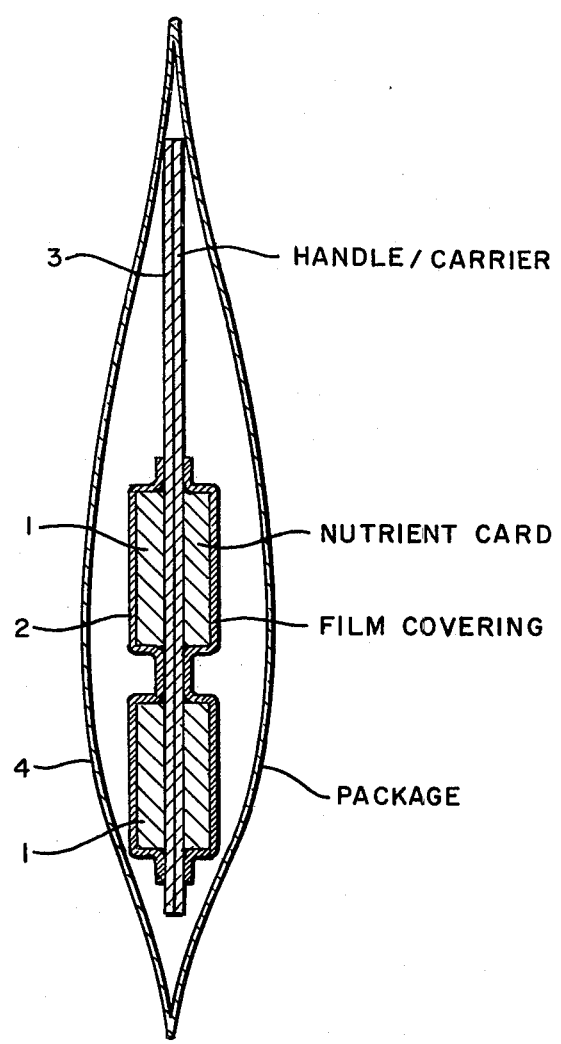
FIG. 2 is a cross-sectional view of the device shown in FIG. 1 also showing a package 4 surrounding the device.

With reference to FIGS. 1 and 2 of the drawing, onto a 200μ thick foil with the dimensions of 2×12 cm. (handle/carrier 3) there are now successively laid two nutrient cards 1 with the dimensions of 2×2 cm. containing Ca-So medium and MacConkey's medium. Over the two nutrient cards is laid the film 2 and attached thereto by sticking onto the foil 3. A second test strip is produced according to the process just described in which, as nutrient media, there are used nutrient cards with Pseudomonas elective and Entrococci selective media. The two test strips are stuck together to give a double sided test strip (FIG. 2). In order to protect the test strip against contamination and moisture, it is individually sealed, for example, with polyethylene-coated paper 4 and sterilized in known manner (FIG. 2). For the detection of micro-organisms in urine, the test strip is removed from the packing 4, dipped into fresh middle stream urine and incubated in an incubation vessel for 12 to 24 hours at 37° C. The pathogenic micro-organisms present in the urine manifest, on such a test strip, the same growth behavior as on the well-known agar nutrient.

FIG. 1 of the drawing illustrates a view of a test strip according to the present invention with two test zones comprising nutrient cards, a film lying thereover and a foil 3 serving as handle and substrate.

FIG. 2 of the drawing is a side view of an individually sealed test strip according to the present invention which has two test zones on the front and on the rear side. As in FIG. 1, this double sided test strip comprises nutrient cards, films and a gripping foil or handle, as well as a packing in which the strip is sealed.

EXAMPLE 3

Determination and differentiation of micro-organisms

Films produced in the manner described in Example 1 are cut up into squares with 5 cm. long sides.

Nutrient cards of the same size are laid in a Petri dish and moistened with sterile water. As nutrient media, there can be used all nutrient and nutrient-inhibitor compositions known in microbiology.

For the determination of the micro-organism count, it is best to use a universal medium, for example the Ca-So medium. For micro-organism differentiation, there is used an elective or selective medium, for example MacConkey's medium for the substantial inhibition of the gram-positive flora, Slanetz and Bartley's enterococcal-selective medium, Pseudomonas elective medium, Wilson and Blair's Salmonella selective medium and the like.

On to the moistened nutrient cards are laid films, the wetting agents of which are chosen in such a manner that they are compatible with the nutrient medium and a precisely pipetted amount of micro-organism suspension distributed thereon with a spatula.

After an incubation period of 12 to 48 hours at 30° to 37° C., by counting the colonies, the micro-organism count can be determined and, by the growth behaviour of the micro-organisms on the various media, the type thereof can be identified.

EXAMPLE 4

Diagnosis of urinary infections

For the diagnosis of a urinary infection, use is made of a test strip according to Example 1. The wetting agent of the film is, as in Example 3, coordinated with the nutrient medium. For this purpose, a nutrient card is cut with the dimensions of 2.5×2.5 cm., laid on a 2.5×10 cm. sealing foil and the film sealed with a hot-seal roller in such a manner that it lies close to the nutrient card. It is preferable to employ one nutrient card with CLED medium and one with MacConkey medium, which are placed side by side. When such a test strip is dipped into a freshly excreted middle stream of urine and then incubated, there are found for all pathogenic micro-organisms in the urine, especially Colibacteria, Enterococci, *Proteus mirabilis, Proteus vulgaris, Proteus morganii, Proteus rettgeri, Pseudomonas aeruginosa, Candida albicans,* Klebsiella, *Aerobacter aerogenes,* Staphilococcus aureus and Citrobacter, the same results as with the well-known nutrient agar. The great advantage of the new test system in comparison with agar is that the test strips are packed in a sterile manner, can be stored for years and only require a fraction of the storage space needed for agar tests and, in addition, destruction thereof by incineration is less laborious.

EXAMPLE 5

Preparation of antibiograms

In order to test the resistance behaviour of micro-organisms cultured according to Example 4, the following procedure is used:

The usual procedure is employed in which colonies are inoculated with a loop, slurried in sterile physiological sodium chloride solution and 0.1 ml. thereof further worked up. For this purpose, a round nutrient card, for example containing Muller-Hinton's medium, is moistened with sterile water, covered with a film of the same size, the suspension of micro-organisms spread thereon with a spatula and an antibiotic test leaflet according to German Industrial Standard No. 58940 laid thereon. In contradistinction to nutrient agar, it is not necessary to press on the test leaflet since this itself adheres to the moist surface of the test strip. After incubation, for all pathogenic micro-organisms of the urine there are observed, in the case of all antibiotics used, a resistance behaviour which is identical with incubation in normal agar nutrient substrates.

EXAMPLE 6

Determination of the minimum inhibiting concentration 62 g. of a dispersion of a co-polymer of vinyl acetate and vinyl propionate, 16 g. polyvinylpyrrolidone dissolved in 22 ml. water, 1 ml. of the phosphate buffer described in Example 1 and 1 g. polyethylene sorbitan monooleate are stirred until homogeneous and the pH value adjusted to 7.3 with aqueous sodium hydroxide solution. Into this film mass are stirred the antibiotics according to German Industrial Standard No. 58940 in increasing amounts, namely, 2.0 $\mu$g., 20 $\mu$g., 200 $\mu$g., 2.0 mg. and 20 mg. per 100 g.

The crude masses thus produced are, as described in Example 2, coated with a layer thickness of 350$\mu$ on to a nylon mesh of about 60$\mu$ thickness and 40$\mu$ filament thickness and subsequently dried at 50° C. Test strips are produced from the "antiobiotic films" thus obtained. For this purpose, on to a stiff foil there is laid a 2.5×2.5 cm. nutrient card with Ca-So medium. Over the nutrient card there is sealed the "antibiotic films." There can be produced test strips for each antibiotic and each concentration or on to one test strip there can be applied films with various concentrations of the same antibiotic.

If these test strips are dipped, for example, into micro-organism-containing urines or if micro-organism suspensions are applied to the test zones, followed by incubation in known manner, the minimum inhibiting concentration can be determined without difficulty and from this the resistance of the micro-organism can be assessed and the correct therapeutic procedure instituted.

Determinations of the minimum inhibiting concentration carried out parallel thereto according to the well-known process using nutrient broth with subsequent nephelometric evaluation showed that the same therapeutic consequences are provided by the results of the process according to the present invention and from the well-known process.

EXAMPLE 7

Determination of the minimum inhibiting concentration of antibiotics which are more stable in another pH range than in the pH range of optimum micro-organism growth (a) Double film based on a dispersion It is known that, for example, cephazolin is stable in a pH range of from 5.2 to 5.6 for a comparatively longer period of time than in the pH range of from 7.0 to 7.5, i.e. the pH range for the optimum growth of pathogenic micro-organisms in urine. In this case, double films are produced in the following manner:

On to an antibiotic-free film according to Example 2 there is coated, in a layer thickness of 35$\mu$, a crude film mass according to Example 6 which has been adjusted with aqueous sodium hydroxide solution to a pH value of 5.2 to 5.6 and into which has been stirred increasing amounts of cephazolin, the following amounts of antibiotic per 100 g. crude film mass thereby being stirred in: 20 $\mu$g., 200 $\mu$g., 2.0 mg., 20 mg. and 200 mg.

The further working up, drying and production of the test strips, as well as the testing of the resistance behaviour of the micro-organisms in urine and of suspensions of micro-organisms is carried out in the manner described in Example 6.

Determinations of the minimum inhibiting concentration carried out parallel thereto according to the well-known processes gave the same results, as described in Example 6.

"Double-layer films" produced in this manner showed, even after 12 months, more than 95% of the activity of the cephazolin contained therein, whereas a film in which the cephazolin was present at a pH of 7.0 had already lost over 50% of its activity.

(b) Double film from film formers which are not dispersions

The second, antibiotic-containing film can, instead of being produced from a dispersion, also be made from a film former which liberates the antibiotic during the incubation phase but which is not a dispersion.

20 g. Homopolymeric ethylene oxide are dissolved in sufficient water to give 100 ml. To this is added 1 g. polyoxyethylene sorbitan oleate. The solution is adjusted with hydrochloric acid to the necessary pH value of 5.2 to 5.6, the amounts of cephazolin mentioned in Example 7(a) are added thereto and the mixture is stirred until homogeneous.

Further working up and the results obtained with such tests are the same as those described in Example 7(a).

EXAMPLE 8

Test strips in which, in addition to macromolecular openers, nutrient materials are present in the film 62 g. of a dispersion of a co-polymer of vinyl acetate and vinyl propionate are mixed with 37 g. of a solution composed of 37 g. polyvinylpyrrolidone, 13.0 g. disodium hydrogen phosphate and 2.3 g. potassium dihydrogen phosphate in 500 ml. water into which are stirred 2.0 g. lactose and 1.0 g. polyoxyethylene sorbitan monooleate.

Films are produced from the crude film in the manner described in Example 2 and, as there described, test strips are produced by combination with a nutrient card which is impregnated with a universal medium.

On such test strips, pathogenic micro-organisms of the urine show, in some cases, much better formed colonies than on the well-known agar nutrient media.

EXAMPLE 9

Test strips in which only nutrients are added to the film as pore formers

A curde film mass is prepared with the following composition: into 100 g. of a dispersion of a co-polymer of vinyl acetate and vinyl propionate are stirred 10 ml. of 0.7 M phosphate buffer in which are dissolved 1.5 g. glucose and 1.5 g. lactose. Thereafter, 1.0 g. polyoxyethylene sorbitan monooleate are stirred in and the crude film mass is adjusted to a pH of 7.3 with aqueous sodium hydroxide solution.

Test strips are produced with this crude film mass in the manner described in Example 8.

Of the pathogenic micro-organisms of urine, *Pseudomonas aeruginosa* grows on these test strips considerably better than on most others so that, with this test, it is possible to carry out an orienting examination for this micro-organism.

What is claimed is:

1. Microbiological test device comprising a nutrient card and a covering layer which is impermeable to bacteria but permeable to nutrients, said covering layer comprising a water-insoluble synthetic resin film modified with a pore former which is a water-soluble or water-swellable compound, said film having been produced from an aqueous dispersion of the synthetic resin and wherein the pore former and resin film have no negative effect on bacterial growth.

2. Test device of claim 1 wherein the pore former is a polyethylene glycol, polyethylene oxide, polyvinylpyrrolidone, polyvinyl alcohol, partly saponified polyvinyl ester, a copolymer of vinylpyrrolidone and a vinyl ester or a cellulose derivative.

3. Test device of claim 2 wherein the cellulose derivative used as a pore former is a hydroxyalkylcellulose.

4. Test device of claim 1 wherein the synthetic resin film is a homopolymer of vinyl acetate or of an acrylic acid ester, a co-polymer of vinyl propionate and vinyl acetate, vinyl propionate and vinyl chloride, vinyl acetate and a maleic acid ester, an acrylic acid ester with acrylonitrile and vinyl propionate and butadiene and styrene.

5. Test device of claim 1 wherein the synthetic resin film has a thickness of from 10 to 1000μ.

6. Test device of claim 1 wherein the weight ratio of pore former to synthetic resin is from 5:1 to 1:50.

7. Test device of claim 1 wherein the film contains a synthetic resin mesh.

8. Test device of claim 7 wherein the synthetic resin mesh has a thickness of from 10 to 200μ.

9. Test device of claim 7 wherein the synthetic resin mesh is provided with colored markings at definite distances apart.

10. Test device of claim 1 wherein the covering layer contains at least one wetting agent, buffer, salt and/or nutrient.

11. Test device of claim 10 wherein the additional materials in the covering layer account for 0 to 15% of the weight thereof.

12. Test device of claim 1 wherein the covering layer contains at least one substance which inhibits and/or promotes the growth of particular micro-organisms.

13. Test device of claim 12 wherein the covering layer contains an antibiotic.

14. Test device of claim 1 wherein the nutrient card is a filtered paper impregnated with a nutrient solution conventionally used in microbiology.

15. Test device of claim 1 wherein the nutrient card contains at least one wetting agent, moisture-retaining agent, swelling agent, buffer, salt and/or antibiotic.

16. Test device of claim 1 wherein the nutrient card is attached to a water-resistant support.

17. Test device of claim 16 wherein the nutrient card is fixed in a pocket formed by the support and the covering layer.

18. Test device of claim 17 wherein the pocket is formed by adhering or sealing projecting edges of the covering layer adjacent to the nutrient card onto the support.

19. Test device of claim 16 wherein the support is provided with an elongation which serves as a handle.

20. Test device of claim 16 wherein the support is made of a synthetic resin foil.

21. Test device of claim 16 wherein a plurality of covering layers and/or nutrient cards of different composition are fixed to the support.

22. Test device of claim 21 wherein the compositions differ in the concentration of an antibiotic.

23. Method for determining micro-organism counts and for the differentiation of micro-organisms which comprises dipping a test device of claim 1 into a liquid to be investigated, wiping off excess liquid, incubating the device and counting the colonies of micro-organisms formed or differentiating the types of micro-organisms by the growth behavior thereof on various media.

24. Method of producing an antibiogram which comprises moistening a test device of claim 1 with a suspension of micro-organisms, depositing an antibiotic test leaflet thereon, incubating the device and thereafter determining the resistance behavior.

25. Method for the determination of the minimum inhibiting concentration of an antibiotic using a test device of claim 1, wherein the covering layer and/or nutrient card contains definite concentrations of the antibiotic, dipping the test device into a suspension of microorganisms, incubating the device and determining, the minimum inhibitor concentration which prevents the growth of the microorganisms.

* * * * *